United States Patent [19]

Cucinella

[11] 4,299,986
[45] Nov. 10, 1981

[54] METHOD OF REDUCING ORGANIC COMPOUNDS WITH MIXED HYDRIDE ALKOXY DERIVATIVES OF ALUMINUM AND ALKALINE EARTH METALS

[75] Inventor: Salvatore Cucinella, San Donato Milanese, Italy

[73] Assignee: Anic, S.p.A., Palermo, Italy

[21] Appl. No.: 104,809

[22] Filed: Dec. 18, 1979

Related U.S. Application Data

[62] Division of Ser. No. 960,781, Nov. 15, 1978, Pat. No. 4,219,491.

[51] Int. Cl.$^3$ .............................................. C07F 9/50
[52] U.S. Cl. ...................................... 568/8; 568/846; 568/862; 568/880; 585/400
[58] Field of Search ..................... 260/606.5 P; 568/8, 568/17, 846, 862, 880; 585/400

[56] References Cited

U.S. PATENT DOCUMENTS

| | | | |
|---|---|---|---|
| 3,031,509 | 4/1962 | Marshall et al. | 260/606.5 P |
| 3,060,216 | 10/1962 | Hamprecht et al. | 260/448 AD |
| 3,147,272 | 9/1964 | Brown et al. | 260/448 AD X |
| 3,281,443 | 10/1966 | Hunt | 260/448 AD |
| 3,933,879 | 1/1976 | Langer et al. | 260/606.5 P X |
| 4,053,521 | 10/1977 | Giongo et al. | 260/606.5 P |
| 4,113,783 | 9/1978 | Malpass | 260/606.5 P |

OTHER PUBLICATIONS

Isslieb et al., Leitschrift fur Anorganische und Allgemeine Chemie 299 58 (1959) (Abstract).

*Primary Examiner*—Helen M. S. Sneed
*Attorney, Agent, or Firm*—Morgan, Finnegan, Pine, Foley & Lee

[57] ABSTRACT

Mixed alkoxy-hydride derivatives of aluminum and alkaline-earth metals are disclosed having the formula $$M[AlH_{4-n}(OR)_n]_2$$

which may be complexed with a Lewis base wherein M is an alkaline-earth metal, R is selected from an aliphatic, cycloaliphatic or aromatic group having from 1 to 20 carbon atoms and n is a number between 0.5 and 3.5. There is also disclosed a novel process for preparing said derivatives which are useful as reducing agents.

5 Claims, No Drawings

METHOD OF REDUCING ORGANIC COMPOUNDS WITH MIXED HYDRIDE ALKOXY DERIVATIVES OF ALUMINUM AND ALKALINE EARTH METALS

This is a divisional application of Ser. No. 960,781 filed on Nov. 15, 1978 now U.S. Pat. No. 4,219,491 and claims the priority of Italian Patent Application No. 29752 A/77 filed on Nov. 17, 1977.

This invention relates to a method for the synthesis of novel compounds of aluminum and alkaline-earth metals, containing hydride hydrogens and alkoxy radicals, such compounds having the composition:

$$M[AlH_{4-n}(OR)_n]_2 \quad (I)$$

wherein $0.5 \leq n \leq 3.5$, OR is an alkoxy radical derived from a primary, secondary or tertiary alcohol, R is an aliphatic, cycloaliphatic or aromatic hydrocarbonaceous radical. The compounds outlined above, which are another object of the present invention, find their particular application as reducing agents in organic chemistry. They reduce ketones to secondary alcohols, aldehydes to primary alcohols, the acids, the esters, anhydrides and the acidic chlorides into alcohols, amides to amines, the sulfoxides to sulfides, phosphine oxides to phosphine and so on. The presence, in such compounds, of alkoxy-hydride the nature of aluminum and alkaline-earth metals and of an optically active radical R, moreover, makes it possible to hydrogenate prochiral substrates to products which are also provided with an optical activity.

The hydrogenation reaction, as a rule, is generally carried out in an inert organic solvent, such as an ethereal or aromatic of aliphatic hydrocarbonaceous solvent, using stoichiometric amounts or an excess of a derivative (I) with respect to the organic function to be reduced. The reaction then proceeds through the formation of an interaction compound between the reducing agent and the substrate. Eventually, the hydrolysis of the reaction mixture produces the expected reduction product, the alcohol which corresponds to the alkoxy radical of (I) and the hydroxides of the aluminum and of the alkaline-earth metal concerned.

The use in the practice of organic chemistry of a few hydride compounds of aluminum or boron and their complexed compounds with iodides of alkali metals is known in the literature. It is likewise known that each of these compounds imposes certain limitations as to the mode of use and/or reactivity towards the several organic substrates. For example, lithium aluminum hydride is a strongly active reagent which is capable of reducing many a functional group, but it is also very reactive when in contact with air and moisture, with the hazard of violent decompositions and explosions; in addition, its solubility is restricted to the ethereal solvents only. On the other hand, NaBH$_4$ is a reagent which is comparatively much safer, but its poor reactivity limits its use to the reduction of carbonyl functions and of acidic chlorides in an aqueous or an alcoholic solution. Few other compounds have properties intermediate between those of LiAlH$_4$ and NaBH$_4$, or display, additionally, different properties: in spite of this, they still have quite particular inherent defects. For example, Li(iso-C$_4$H$_9$)$_2$H and NaAl(C$_2$H$_5$)$_2$H$_2$ contain, for every one or two hydride hydrogens, two expansive Al—R groups, respectively and these, if they do not originate undesirable side reactions, remain unused and thus contribute towards rendering the final hydrolysis reaction both difficult and hazardous due to the extreme reactivity of the aluminum-carbon bond towards water and other hydrolysis agents. Although a great number of hydride derivatives of aluminum (or of boron) have been synthesized and identified, the chemical and physical properties of many of them have proven to be unfavorable for use as reducing agents in the practice of organic chemistry. For example, the literature has widely described the synthesis of Ca(AlH$_4$)$_2$ and of Mg(AlH$_4$)$_2$ [A. E. Finholt, USP 2 550 985, W. Schwab and K. Wintersberger, Zeit. Naturforsch., B, 8, 690 (1953), E. C. Ashby, Adv. Inorg. Chem. Radiochem., 8, 327 (1966), E. C. Ashby, R. D. Schwartz and B. D. James, Inorg. Chem., 9, 325 (1970)]. These compounds are generally obtained in the form of their complexes with tetrahydrofuran. These compounds, however, have not been paid attention to as a reducing agents, mainly due to their poor solubilities in the organic solvents. Ca(AlH$_4$)$_2$ is soluble in tetrahydrofuran, but is insoluble in other solvents (ethereal) and in hydrocarbons, while Mg(AlH$_4$)$_2$ is insoluble also in tetrahydrofuran. While it is quite true that the reaction of Ca(AlH$_4$)$_2$ (or of Mg(AlH$_4$)$_2$) with primary amines has made it possible to synthesize poly(N-alkyl-imino derivatives (mixed) of aluminum and alkaline-earth metals which are more soluble, but such compounds, when used as reducing agents in organic chemistry, may give rise to undesirable side reactions for which the Al—NR bonds are responsible due to their reactivity, so that, for example, in the hydrogenation of organic acids and their derivatives, the formation of amide derivatives may overwhelm the formation of the alcohol. We have now found that the reaction of the compounds having the general formula M(AlH$_4$)$_2$M (M is an alkaline earth metal) with an aliphatic, cycloaliphatic, or aromatic alcohol, be it a primary, a secondary or a tertiary alcohol, gives rise to the formation of derivatives which are, as a rule, soluble in the ethereal solvents and in the aromatic hydrocarbons and, in certain cases, consistently with the natural of the alkoxy radical, they are soluble also in aliphatic hydrocarbons. The reaction pattern can be written as follows:

$$M(AlH_4)_2 + 2nROH \rightarrow M[AlH_{4-n}(OR)_n]_2 + 2\,nH_2 \quad (1)$$

wherein $0.5 \leq n \leq 3.5$.

Compounds of this kind have a considerable heat stability and are age-resistant and, in contact with air and moisture, they become with moderate reactions without any hazard of abrupt decomposition.

The products in question are generally solid, so that they, apart from the expedient of blanketing them with an inert gas, do not give rise to any special problems as to storage, packaging, shipping and dose-metering and handling at large, and can immediately be solubilized prior to employing the solvent which has been deemed most suitable for the kind of reaction which is to be carried into effect.

The selection of an appropriate alkoxy group in (I) enables, in the final hydrolysis, a corresponding alcohol to be obtained, which has a boiling point temperature distant from that of the expected reduction product, so that complications are avoided in the separation of the latter.

The reaction for synthesizing the compounds which are the subject matter of the present invention requires the use, as reactants, of hydride compounds of the type $M(AlH_4)_2$, which may form a complex with Lewis base. Examples of such compounds are $Ca(AlH_4)_2 \cdot 4THF$, $Mg(AlH_4)_2 6THF$ and others (THF=tetrahydrofuran).

Examples of alcohols which can be used for the synthesis of the compounds in question herein, according to the reaction pattern (1), are: nor. propyl alcohol, nor. butyl alcohol, isobutyl alcohol, nor.amyl alcohol, isoamyl alcohol, nor.octyl alcohol, 2-ethyl-hexyl alcohol, isopropyl alcohol, sec.butyl alcohol, tert.amyl alcohol, cyclohexyl alcohol, and benzyl alcohol. Alcohols may also be used, which contain in their chain other functional groups, such as ethereal, amine, phosphine groups and others, which may possible also interact with the aluminum atoms and/or with the atoms of the alkaline-earth metal, for example with the formation of intramolecular or intermolecular compounds: they could also partially react with the hydride hydrogens without causing them to disappear, however. Examples of such alcohols are, for example, the alkoxyalcohols of the formula $RO(CH_2)_n—OH$ in which n is equal to, or greater, than 1.

The synthesis reaction is carried out in an ethereal or a hydrocarbonaceous solvent selected, for example, from among diethylether, tetrahydrofuran, dioxan, benzene, toluene, pentane, hexane, heptane and others.

The reaction is carried out at a temperature between $-40°$ C. and the temperature of decomposition of the product and preferably between 15° C. and 100° C. in an inert atmosphere. The reaction is not significantly influenced by the pressure within the temperature limits aforesaid. The compounds in question can be obtained and used also in the form of complexes with Lewis' bases, such as with tetrahydrofuran.

The ensuing examples illustrate the invention without limiting it.

EXAMPLE 1

Preparation of $Ca\{AlH_2[OCH(CH_3)_2]_2\}_2 \cdot THF$

To a stirred suspension of $Ca(AlH_2)_2.4THF$ (26.1 millimol) in toluene (150 mls) there is slowly added a solution of isopropyl alcohol (104.4 millimol) in toluene (43 mls).

The reaction is exothermic so that the temperature rises and the velocity of addition is adjusted so that the temperature rise does not exceed 10° C. (differential value) starting from 22° C. Hydrogen evolution is observed.

On completion of the reaction the mixture is carried for 2 hours and allowed to stand for 15 hours. From the resultant solution, upon filtering off the turbid matters, the solvent is distilled off under reduced pressures, the solid residue is dried for about 4 hrs. at about $1.10^{-4}$ Torr at ambient temperature and analyzed.

Found: Al%: 13.0—Ca%: 10.1—$H_{(active)}$ 9 milliequivalents per gram—Calculated, for $C_{16}H_{40}Al_2Ca\ O_5$: Al: 13.3—Ca%: 9.9—$H_{(active)}$ 9.9 meq/g: The yield is quantitative.

The compound is soluble in ethereal solvents and in aromatic hydrocarbons. It is amorphous as examined with X-rays. By heating, it begins to decompose (slowly) at about 150° C. The decomposition proceeds swiftly at about 240° C. The ebullioscopic mol wt in diethylether is 420 (calcd. 406.5). The $^1H$ NMR spectrum in benzene at 70° C. shows a doublet at $\tau 7.92$ due to the group $CH_3$ and a heptet at $\tau 5.08$ due to the CH group of magnetically equivalent isopropyl radicals.

EXAMPLE 2

Preparation of $Ca\{AlH_2\ [OCH_2CH_2—CH(CH_3)_2]_2\}_2$

To a stirred suspension of $Ca(AlH_4)_2.4THF$ (27.2 millimols) in toluene (100 mls) there is added slowly a solution of isoamyl alcohol (108.8 millimols) in toluene (38 mls). The reaction is exothermic and the velocity of addition is so adjusted that the temperature rise does not exceed 10° C. (difference) starting from 20° C. Gas evolution is experienced. On completion, the mixture is stirred for 1 hr and then allowed to stand 15 hrs. From the resultant solution, upon filtration to discard insolubles, the solvent is distilled off under reduced pressures and the oily residue is dried for 10 hrs. under a pressure of about $1.10^{-4}$ Torr and at room temperature to give a solid which is analyzed.

Found: Al%=11.9; Ca%=9.5; $H_{(active)}$ 8.7 meq/g; Calcd.: for $C_{20}H_{48}Al_2Ca\ O_4$: Al%=12.1; Ca%=9.0; $H_{(active)}$ 9.0 meq/g.

The yield is 80%. The compound is soluble in tetrahydrofuran and in aromatic hydrocarbons. It is amorphous when examined with X-rays. When heated, it begins to decompose at 150° C.

EXAMPLE 3

Preparation of $Ca\ [AlH_2(OC_6H_{11})_2]_2 \cdot THF$

To a stirred solution of $Ca(AlH_4)_2.4THF$ (13.5 millimols) in toluene (50 mls) there is slowly added a solution of cyclohexyl alcohol (54.1 millimols) in toluene (20 mls).

The reaction is exothermic and the velocity of addition is adjusted so that the temperature rise does not exceed 15° C. starting from 22° C. Hydrogen evolution is experienced. On completion of the reaction, the mixture is stirred for 1 hour 30 mins. and then allowed to stand 15 hrs. The reaction is then finished by refluxing for 2 hrs 30 mins., and a slightly turbid solution is obtained. The impurities are filtered off and the solvent is distilled off under reduced pressures. The solid residue is dried for 10 hrs. under a pressure of about $1.10^{-4}$ Torr at room temperature and analyzed:

Found: Al%=9.3; Ca%=7.0; $H_{(active)}$=6.9 meq/g: Calculated for $C_{28}H_{56}Al_2Ca\ O_5$: Al%=9.5; Ca%=7.1; $H_{(active)}$=7.1 meq/g.

The yield is virtually quantitative. The compound is soluble in ethereal solvents and in aromatic hydrocarbons. It is crystalline when examined with X-rays. Upon heating, it begins slowly to decompose at about 150° C. The ebullioscopic mol wt in diethyl ether is 588 (calculated 566.8).

EXAMPLE 4

Preparation of $Ca\{AlH_2[OC(CH_3)_3]_2\}_2 \cdot THF$

To a stirred solution of $Ca(AlH_4)_2.4THF$ (23.5 millimols) in toluene (130 mls) there is slowly added a solution of tert.butyl alcohol (95 millimols) in toluene (50 mls). The reaction is exothermic and the velocity of addition is adjusted so as to have a temperature rise not in excess of 13° C. starting from 22° C. Hydrogen evolution is experienced. On completion of the addition, the mixture is stirred for 6 hours at room temperature. The impurities are filtered off and the solvent is distilled off the solution under reduced pressures. The solid residue is dried for 15 hrs under a pressure of about $1.10^{-4}$ Torr at room temperature and analyzed:

Found: Al%=11.1; Ca%=8.1; H$_{(active)}$ 8.6 meq/g: Calculated for: C$_{20}$H$_{48}$Al$_2$Ca O$_5$: Al%=11.7; Ca%=8.7; H$_{(active)}$ 8.7 meq/g.

The yield is virtually quantitative. The compound is soluble in ethereal solvents and in aromatic hydrocarbons. It is crystalline under X-ray examination. Upon heating, immediate decomposition is experienced at about 165° C. The ebullioscopic mol wt in diethyl ether is 454 (calculated 462.6).

EXAMPLE 5

Preparation of Ca[AlH$_2$(OC$_8$H$_{17}$)$_2$]$_2$

To a stirred suspension of Ca(AlH$_4$)$_2$.4THF (26.5 millimols) in toluene (130 mls) there is added slowly a solution of 2-ethyl-hexanol (106 millimols) in toluene (50 mls). The reaction is exothermic and the velocity of addition is so adjusted that the rise of the temperature does not exceed 12° C. starting from 21° C. Hydrogen evolution takes place. On completion of the addition the mixture is stirred for 2 hrs. The impurities are filtered off and the solvent is distilled off under reduced pressures. An oily product is obtained, which is dried for 8 hours under a pressure of 1.10$^{-4}$ Torr at room temperature and redissolved in benzene. The benzene solution is then analyzed and the following atomic ratios are observed:

Ca/Al=0.51; H$_{(active)}$/Al=1.85.

The yield is virtually quantitative. The product is soluble in ethereal solvents and in both aromatic and aliphatic hydrocarbons.

EXAMPLE 6

Preparation of Ca [AlH$_2$(OCH$_2$CH$_2$OCH$_3$)$_2$]$_2$

To a stirred solution of Ca(AlH$_4$)$_2$.4THF (26.2 millimols) in toluene (160 mls) there is added slowly a solution of 2-methoxyethanol (104.8 millimols) in toluene (60 mls). The reaction is exothermic and the velocity of addition is so adjusted that the temperature rise never exceeds 15° C. starting from 21° C. Evolution of hydrogen is experienced. Eventually, the solution is stirred for 2 hours, the insolubles are filtered off and the solvent is driven off the solution under reduced pressures. The solid residue is dried under about 1.10$^{-4}$ Torr at room temperature for 8 hrs. and analyzed:

Found: Al%=13.4; Ca%=9.5; H$_{(active)}$ 9.8 meq/g: Calculated for: C$_{12}$H$_{32}$Al$_2$Ca O$_8$:Al% 13.5; Ca% 10.1; H$_{(active)}$ 10.1 meq/g.

The yield is 78%. The compound is soluble in ethereal solvents and aromatic hydrocarbons. It is crystalline when examined with X-rays. Upon heating it begins to decompose at 150° C. The ebullioscopic mol wt in diethyl ether is 506 (calculated 398.4). The $^1$H NMR spectrum in benzene at 70° C. shows a singlet at τ6.03 due to the group —O—CH$_3$ and two triplets at τ6.31 and τ5.68 due to the methylenes —CH$_2$—CH$_2$— of magnetically equivalent 2-methoxyethyl radicals.

EXAMPLE 7

Preparation of Ca{AlH$_{2.5}$[OCH(CH$_3$)$_2$]$_{1.5}$}$_2$.THF

To a stirred solution of Ca(AlH$_4$)$_2$.4THF (25.6 millimos) in toluene (130 mls) there is slowly added a solution of isopropyl alcohol (76.8 millimols) in toluene (65 mls). The reaction is exothermic and the velocity of addition is adjusted so that the rise of the temperature does not exceed 10° C. starting from 21° C. Hydrogen evolution is experienced. On completion of the additions, the mixture is stirred for 2 hours at room temperature. The impurities are filtered off and the solvent is removed from the solution by distillation under reduced pressures. The white solid residue is dried under about 1.10$^{-4}$ Torr at room temperature for 15 hrs., and analyzed:

Found: Al% 15.9; Ca% 12.5; H$_{(active)}$ 14.1meq/g: Calculated for: C$_{13}$H$_{34}$Al$_2$CaO$_4$: Al% 15.5; Ca% 11.5; H$_{(active)}$ 14.5 meq/g.

The yield is quantitative. The compound is soluble in tetrahydrofuran and in aromatic hydrocarbons. The compound is amorphous when examined under X-ray.

EXAMPLE 8

Preparation of Mg[AlH$_2$(OCH$_2$CH$_2$OCH$_3$)$_2$]$_2$

To a stirred solution of Mg(AlH$_4$)$_2$.6THF (48.8 millimols) in tetrahydrofuran (100 mls) there is slowly added a solution of 2-ethoxyethyl alcohol (195.2 millimols) in tetrahydrofuran (85 mls).

The reaction is exothermic and the velocity of addition is adjusted so as to have a temperature rise not in excess of 12° C. starting from 18° C. Hydrogen evolution takes place. On completion of the additions the mixture is stirred for 2 hrs. at room temperature and then refluxed for 6 hours 30 mins. The insolubles are filtered off and the solution is evaporated under reduced pressures. A solid residue is obtained, which is redissolved in toluene and the solvent is distilled off from the solution again under vacuum. The solid is dried for 3 hrs. under 1.10$^{-3}$ Torr and analyzed:

Found: Al% 12.7; Mg% 5.7; H$_{(active)}$ 8.8 meq/g: Calculated for: C$_{12}$H$_{32}$Al$_2$MgO$_8$: Al% 14.1; Mg% 6.3; H$_{(active)}$ 10.5 meq/g.

The yield is 60%. The compound is soluble in aromatic hydrocarbons and is amorphous when examined under X-rays. Upon heating, immediate decomposition is observed at about 150° C. The $^1$H NMR spectrum in benzene at 70° C. shows a singlet at τ6.10 due to the —O—CH$_3$ group and two triplets at τ about 6 and τ5.56 due to the methylenes, —CH$_2$—CH$_2$— of 2-methoxyethyl radicals which are magnetically equivalent.

EXAMPLE 9

Preparation of Mg[AlH$_2$(OC$_6$H$_{11}$)$_2$]$_2$.2THF

To a stirred solution of Mg(AlH$_4$)$_2$.6THF (45.9 millimols) in toluene (100 mls) there is slowly added a solution of cyclohexanol (183.6 millimols) in toluene (30 mls). The reaction is exothermic and the velocity of the addition is so adjusted that the temperature rise never exceeds 14° C. starting from 19° C. Hydrogen evolution takes place. On completion of the addition the mixture is stirred for 3 hrs. at room temperature. A clear solution is obtained, from which the solvent is distilled off under reduced pressures. The white solid residue is dried at about 1.10$^{-4}$ Torr for for 6 hrs. at room temperature and analyzed:

Found: Al% 8.7; Mg% 4.2; H$_{(active)}$ 6.5 meq/g: Calculated for: C$_{32}$H$_{64}$Al$_2$MgO$_6$: Al% 8.7; Mg% 3.9; H$_{(active)}$ 6.5 meq/g.

The yield is quantitative. The compound is soluble in ethereal solvents and in aromatic hydrocarbons. It is crystalline when examined under X-rays. Upon heating, it begins to decompose at about 150° C.

EXAMPLE 10

Preparation of Mg{AlH$_2$[OC(CH$_3$)$_3$]$_2$}$_2$.THF

To a stirred solution of Mg(AlH$_4$)$_2$.6THF(29.7 millimols) in toluene (100 mls) there is slowly added a solution of tert.butyl alcohol (118.8 millimols) in toluene (50 mls). The reaction is exothermic and the velocity of addition is so adjusted that the rise of temperature never exceeds 13° C. starting from 19° C. Hydrogen evolution is experienced. On completion of the addition the mixture is stirred for 5 hrs. at room temperature. The impurities are filtered off and the solvent distilled off from the solution under reduced pressures. The white solid residue is dried under about 1.10$^{-4}$ Torr at room temperature for 15 hrs. and taken up with benzene. The analysis of the benzene solution gives the following atomic ratios:

Mg/Al:0.56; H$_{(active)}$/Al=2.07.

The yield is virtually quantitative. The product is soluble in ethyl ether and in aromatic hydrocarbons. It is crystalline when examined under X-rays. Upon heating immediate decomposition is experienced at about 150° C.

EXAMPLE 11

Working in a nitrogen atmosphere, to 1.75 mls of a toluene solution containing 0.375 millimols of Ca[AlH$_2$—(OCH$_2$—CH$_2$OCH$_3$)$_2$]$_2$ which is stirred, there is added at room temperature 1 ml of a toluene solution which contains 1 millimol of non.butyraldehyde: an exothermic reaction is experienced. The mixture is stirred for 30 mins. at room temperature, thereafter, the mixture cooled to about 0° C., and hydrolyzed by adding thereto a few mls of a 6-normal aqueous solution of H$_2$SO$_4$. The solution is allowed to stand and the toluene layer is recovered and, after having been dried on molecular sieves, is analyzed gaschromatographically. The yield or nor.butanol, the reduction product of nor.-butyraldehyde, is quantitative.

EXAMPLE 12

Operating under the same conditions as in EX. 1, 1 millimol of nor.butyraldehyde in nor.hexane (1ml of a 1M soln.) is reacted with 0.375 millimol of: Ca[AlH$_2$(OCH$_2$CH(C$_2$H$_5$)CH$_2$CH$_2$CH$_2$CH$_3$)$_2$]$_2$ in nor.hexane (1.87 mls of a 0.2M soln.) for 30 mins. at room temperature. Upon treating the reaction mixture according to the procedure of Exalmple 1, the resultant solution in hexane is gaschromatographically analyzed. The yield of nor.butanol, which is the reduction product of nor.-butyraldehyde, is quantitative.

EXAMPLE 13

Operating according to the procedure of Example 1, 1 millimol of benzaldehyde in nor.hexane (1 ml of a 1M soln.) is reacted with 0.375 millimol of Ca[AlH$_2$(OCH$_2$—CH(C$_2$H$_5$)CH$_2$CH$_2$—CH$_3$)$_2$]$_2$ in nor.hexane (187 ml of a 0.2M soln.) during 30 mins. at room temperature. Upon treatment of the reaction mixture according to the method of Example 1, the resultant solution in hexane is gaschromatographically analyzed. The yield of benzyl alcohol, the product of the reduction of benzaldehyde, is quantitative.

EXAMPLE 14

Operating according to the procedure of Example 1, 1 millimol of 2-heptanone in toluene (1 ml of a 1M soln.) is reacted with 0.375 millimol of Ca[AlH$_2$(OC$_6$H$_{11}$)$_2$]$_2$.THF in toluene (1.70 ml of a 0.22M soln.) during 30 mins. at room temperature. Upon treatment of the reaction mixture according to the method of Example 1, the resultant solution in toluene is gaschromatographically analyzed. The yield of 2-heptanol, which is the reduction product of 2-heptanone, is quantitative.

EXAMPLE 15

Operating under the conditions of Example 1, 1 millimol of 2-heptanone in toluene (1 ml of a 1M soln.) is reacted with 0.375 millimol of Ca[AlH$_2$(OCH$_2$CH$_2$OCH$_3$)$_2$]$_2$ in toluene (1.78 ml of a 0.21M soln.) during 30 mins. at room temperature. After treating the reaction mixture according to the procedure of Example 1, the resultant toluene solution is gaschromatographically analyzed. The yield of 2-heptanol, the result of the reduction of 2-heptanone, is quantitative.

EXAMPLE 16

Operating according to the procedure of Example 1, 1 millimol of 4-methyl-2-pentanone in toluene (1 ml of a 1M soln.) is reacted with 0.375 millimol of Ca[AlH$_2$(OCH$_2$CH$_2$OCH$_3$)$_2$]$_2$ in toluene (1.78 ml of a 0.21M soln.) during 30 mins. at room temperature. Upon treating the reaction mixture according to the procedure of Example 1, the solution in toluene which is obtained is gaschromatographically analyzed. The yield of 4-methyl-2-pentanol, the reduction product of 4-methyl-2-pentanone, is 99.5%.

EXAMPLE 17

Operating according to the procedure of Example 1, 1 millimol of 4-methyl-2-pentanone in toluene (1 ml of a 1M soln.) is reacted with 0.375 millimol of Mg[AlH$_2$(OC$_6$H$_{11}$)$_2$]$_2$.2THF in toluene(1.78 ml of a 0.21M soln.) for 30 mins. at room temperature. Upon treatment of the reaction mixture according to the procedure of Example 1, the resultant solution in toluene is gaschromatographically analyzed. The yield of 4-methyl-2-pentanol, which is the product of the reduction of 4-methyl-2-pentanone, is 99%.

EXAMPLE 18

Operating according to the procedure of Example 1, 1 millimol of cyclohexanone in toluene (1 ml of a 1M soln.) is reacted with 0.375 millimol of Ca[AlH$_2$(O-tert.C$_4$H$_9$)$_2$]$_2$.THF in toluene (1.5 ml of a 0.25M soln.) for one hour at room temperature. After treating the reaction mixture according to the procedure of Example 1, the resultant solution in toluene is gaschromatographically analyzed. The yield of cyclohexanol, which is the product of the reduction of cyclohexanone, is quantitative.

EXAMPLE 19

Operating according to the procedure of Example 1, 1 millimol of cyclohexanone in toluene (1 ml of a 1M soln.) is reacted with 0.375 millimol of Ca[AlH$_2$(OCH$_2$CH$_2$OCH$_3$)$_2$]$_2$ in toluene (1.78 ml of a 0.21M soln.) during one hour at room temperature. Upon treating the reaction mixture according to the method of Example 1, the resultant solution in toluene is gaschromatographically analyzed. The yield of cyclohexanol, which is the product of the reduction of cyclohexanone, is quantitative.

EXAMPLE 20

Operating according to the procedure of Example 1, 1 millimol of acetophenone in nor.hexane (1 ml of a 1M soln.) is reacted with 0.375 millimol of Ca [AlH$_2$(OCH$_2$-CH(Ch$_2$H$_5$)CH$_2$CH$_2$CH$_2$CH$_3$)$_2$]$_2$ in nor.hexane (1.87 ml of a 0.2M soln.) for 30 mins. at room temperature. Upon treating the reaction mixture according to the method of Example 1, the resultant solution in hexane is gaschromatographically analyzed. The yield of methylphenylcarbinol, which is the product of the reduction of acetophenone, is quantitative.

EXAMPLE 21

Operating according to the method of Example 1, 1 millimol of butyric acid in toluene (1 ml of a 1M soln.) is reacted with 1.125 millimol of Ca [AlH$_2$(OCH$_2$CH$_2$OCH$_3$)$_2$]$_2$ in toluene (5.36 mls of a 0.21M soln.) for 15 hours at room temperature plus 1 hour 30 mins. at 80° C. After the treatment of the reaction mixture according to the procedure of Example 1, the resultant solution in toluene is gaschromatographically analyzed. The yield of nor.butanol, which is the product of the reduction of butyric acid, is a quantitative.

EXAMPLE 22

Operating according to the method of Example 1, 1 millimol of butyric acid in nor.hexane (1 ml of a 1 M soln.) is reacted with 1.125 millimol of Ca[AlH$_2$(OCH$_2$CH(C$_2$H$_5$)CH$_2$CH$_2$CH$_2$CH$_3$)$_2$]$_2$ in nor.hexane (5.62 mls of a 0.2 M soln.) during one hour at room temperature plus 3 hours 30 mins at refluxing temperatures. After the treatment of the reaction mixture according to the procedure of Example 1, the solution in hexane which is obtained is gaschromatographed. The yield of nor.butanol, which is the product of the reduction of butyric acid, is 92%.

EXAMPLE 23

Operating according to the procedure of Example 1, 1 millimol of capronic acid in toluene (1 ml of a 1 M soln.) is reacted with 1 millimol of Ca[AlH$_2$(OC$_6$H$_{11}$)$_2$]$_2$ .THF in toluene (4.54 mls of a 0.22 M soln.) for one hour at room temperature plus 3 hr 30 mins at 85° C. After the treatment of the reaction mixture according to the procedure of Example 1, the resultant solution in toluene is gaschromatographed. The yield of nor.hexanol, the product of the reduction of capronic acid, is quantitative.

EXAMPLE 24

Operating according to the procedure of Example 1, 1 millimol of capronic acid (1 ml of a 1 M soln.) is caused to interact with 1 millimol of Mg[AlH$_2$(OC$_6$H$_{11}$)$_2$]$_2$.2THF in toluene (3.70 mls of a 0.27 M soln.) for 1 hr at room temperature plus 1 hr 30 mins at 80° C. After the treatment of the reaction mixture according to the procedure of Example 1, the resultant solution in toluene is gaschromatographed. The yield of nor. hexanol, which is the product of the reduction of capronic acid, is 99.5%.

EXAMPLE 25

Operating according to the procedure of Example 1, 1 millimol of ethyl butyrate in benzene (1 ml of a 1 M soln.) is reacted with 0.75 millimol of Ca[AlH$_2$(OC$_6$H$_{11}$)$_2$]$_2$.THF in benzene (3.41 ml of a 0.22 M soln.) for one hour at room temperature. Upon treatment of the reaction mixture according to the method of Example 1, the solution in benzene which is thus obtained is gaschromatographed. The yield of nor.butanol, which is the product of the reduction of ethyl butyrate, is quantitative.

EXAMPLE 26

Operating according to the procedure of Example 1, 1 millimol of ethyl butyrate in benzene (1 ml of a 1 M solm.) is reacted with 0.75 millimol of Mg[AlH$_2$(OC$_6$H$_{11}$)$_2$]$_2$.2THF in benzene (2.88 ml of a 0.26 M soln.) for 1 hr at room temperature. Upon treatment of the reaction mixture according to the method of Example 1, the solution in benzene thus obtained is gaschromatographed. The yield of nor.butanol, which is the product of the reduction of ethyl butyrate, is quantitative.

EXAMPLE 27

Operating according to the procedure of Example 1, 1 millimol of ethyl caproate in toluene (1 ml of a 1 M solution) is reacted with 0.75 millimol of Ca[AlH$_2$(O-tert.C$_4$H$_9$)$_2$]$_2$.THF in toluene (3 mls of a 0.25 M soln.) for 1 hr at room temperature. After treating the reaction mixture according to the method of Example 1, the toluene solution which is so obtained is gaschromatographed. The yield of nor.hexanol, which is the product of the reduction of ethyl caproate, is quantitative.

EXAMPLE 28

Operating according to the procedure of Example 1, 1 millimol of ethyl caproate in toluene (1 ml of a 1 M soln.) is reacted with 0.75 millimol of MG[AlH$_2$(OC$_6$H$_{11}$)$_2$]$_2$.2THF in toluene (2.78 mls of a 0.27 M soln.) for 1 hr at room temperature. After the treatment of the reaction mixture according to the procedure of Example 1, the toluene solution which has thus obtained is gaschromatographed. The yield of nor.hexanol, which is the product of the reduction of the ethyl caproate, is quantitative.

EXAMPLE 29

Operating according to the procedure of Example 1, 1 millimol of ethyl cyclohexylacetate in toluene (1 ml of a 1 M soln.) is reacted with 0.75 millimol of Ca[AlH$_2$(OCH$_2$—CH$_2$OCH$_3$)$_2$]$_2$ in toluene (3 mls of a 0.25 M soln.) for 1 hr at room temperature. After the treatment of the reaction mixture according to the method of Example 1, the resultant solution in toluene is gaschromatographed. The yield of 2-cyclohexyl ethanol, which is the product of the reduction of ethyl cyclohexylacetate, is quantitative.

EXAMPLE 30

Operating according to the procedure of Example 1, 1 millimol of ethyl cyclohexylacetate in nor.hexane (1 ml of a 1 M soln.) is reacted with 0.75 millimol of Ca-[AlH$_2$—(OCH$_2$—CH(C$_2$H$_5$)CH$_2$CH$_2$CH$_2$CH$_3$)$_2$]$_2$ in nor.hexane (3.75 mls of a 0.2 M soln.) for 1 hr at room temperature. After the treatment of the reaction mixture with the procedure of Example 1, the resultant solution in toluene is gaschromatographed. The yield of 2-cyclohexyl ethanol, which is the product of the reduction of the ethyl cyclohexylacetate, is quantitative.

EXAMPLE 31

Operating according to the procedure of Example 1, 1 millimol of ethyl benzoate in toluene (1 ml of a 1 M soln.) is reacted with 0.75 millimol of Ca[AlH$_2$(O-tert.C$_4$H$_9$)$_2$]$_2$.THF toluene (3 mls of a 0.25 M soln.) for 1 hr at room temperature. After having treated the reaction mixture with the method of Example 1, the resultant solution in toluene is gaschromatographed. The yield of benzyl alcohol, which is the product of the reduction of ethyl benzoate, is 96.5%.

EXAMPLE 32

Operating according to the procedure of Example 1, 0.82 millimol of ethyl benzoate in toluene (0.82 mls of a 1 M soln.) are treated with 0.65 millimol of Mg[AlH$_2$(OC$_6$H$_{11}$)$_2$]$_2$.2THF in toluene (2.41 mls of a 0.27 M soln.) during 1 hr at room temperature. Upon treatment of the reaction mixture according to the procedure of Example 1, the resultant solution in toluene is gaschromatographed. The yield of benzyl alcohol, which is the product deriving from the reduction of the ethyl benzoate, is 96.5%.

EXAMPLE 33

Operating under a nitrogen atmosphere, to 3 mls of a stirred solution in toluene which contains 0.75 millimol of Ca[AlH$_2$(O-tert.C$_4$H$_9$)$_2$]$_2$.THF there is added slowly at room temperature 1 ml of a toluene solution (conc. 1 M) of 4-butyrolactone. The mixture is stirred for 1 hr at room temperature. Thereafer, decomposition results from the addition of a few drops of water and a few mls of ethanol are added thereto. By filtration a clear solution is separated, which is dried over molecular sieves and gaschromatographed. The yield of 1,4-butanediol, which is the result of the reduction of 4-butyrolactone, is quantitative.

EXAMPLE 34

Operating with the procedure of Example 23, 1 millimol of 4-butyrolactone in toluene (1 ml of a 1 M soln.) is reacted with 0.75 millimols of Mg[AlH$_2$(OC$_6$H$_{11}$)$_2$]$_2$.2THF in toluene (2.78 mls of a 0.27 M soln.) for 1 hr at room temperature. After having treated the reaction mixture according to the method of Example 23, the solution thus obtained is gaschromatographed. The yield of 1.4-butanediol, which is the product of the reduction of 4-butyrolactone, is quantitative.

EXAMPLE 35

Operating according to the method of Example 1, 0.44 millimol of propionic acid anhydride in benzene (0.44 ml of a 1 M solution) is reacted with 0.825 millimol of Ca[AlH$_2$(OC$_6$H$_{11}$)$_2$]$_2$.THF (5.15 mls of a 0.16 M soln.) for 1 hr at room temperature plus 2 hr 30 mins at refluxing temperature. Upon treatment of the reaction mixture according to the procedure of Example 1, the resultant solution in toluene is gaschromatographed. The yield of nor.propyl alcohol, which is the reduction derivative of propionic acid anhydride, is quantitative.

EXAMPLE 36

Operating according to the method of Example 1, 0.53 millimol of pivalic acid anhydride in toluene (0.53 ml of a 1 M soln.) is reacted with 1 millimol of Ca[AlH$_2$(OC$_6$H$_{11}$)$_2$]$_2$.THF (6.25 mls of a 0.16 M soln.) for 1 hr at room temperature plus 1 hr at the refluxing temperature. After the treatment of the mixture of reaction according to the procedure of Example 1, the solution in toluene which is obtained is gaschromatographed. The yield of neopentyl alcohol, which is the product of the reduction of the pivalic acid anhydride, is quantitative.

EXAMPLE 37

Operating according to the method of Example 1, 1 millimol of benzoyl chloride in toluene (1 ml of a 1 M soln.) is reacted with 0.75 millimol of Ca[AlH$_2$(O.-tert.C$_4$H$_9$)$_2$]$_2$.THF in toluene (3 mls of a 0.25 M soln.) for 1 hr at room temperature. After treatment of the reaction mixture according to the method of Example 1, the solution in toluene which is obtained is gaschromatographed. The yield of benzyl alcohol, which is the product of the reduction of the benzoyl chloride, is 95%.

EXAMPLE 38

Operating according to the procedure of Example 1, 1 millimol of benzoyl chloride in toluene (1 ml of a 1 M soln.) is reacted with 0.75 millimol of Mg[AlH$_2$—(OC$_6$H$_{11}$)$_2$]$_2$.2THF in toluene (2.77 mls of a 0.27 M soln.) for 1 hr at room temperature. Upon treatment of the reaction mixture according to the step sequence of Example 1, the toluene solution which is thus obtained is gaschromatographed. The yield of benzyl alcohol, which is the product of the reduction of the benzoyl chloride, is as high as 96.5%.

EXAMPLE 39

Operating according to the procedure of Example 1, 1 millimol of benzyl chloride in benzene (1 ml of a 1 M soln.) is reacted with 0.375 millimol of Ca[AlH$_2$(OC$_6$H$_{11}$)$_2$]$_2$.THF in benzene (2.34 mls of a 0.16 M soln.) for 1 hr at room temperature plus 4 hrs at 80° C. Upon treatment of the reaction mixture according to Example 1, the benzene solution which is obtained is gaschromatographed. The result is that benzyl chloride is converted into toluene with a yield of 55.5%.

EXAMPLE 40

Operating according to the step sequence of Example 1, 1 millimol of chlorobenzene in toluene (1 ml of a 1 M soln.) is reacted with 0.375 millimol of Ca[AlH$_2$(O—tert.C$_4$H$_9$)$_2$]$_2$.THF intoluene (1.5 mls of a 0.25 M soln.) for 1 hr at room temperature. Upon treating the reaction mixture according to the method of Example 1, the toluene solution which is obtained is gaschromatographed. The result is that the chlorobenzene is converted into benzene with a yield of 20%.

I claim:

1. A method of reducing an organic compound selected from the group consisting of ketones, aldehydes, acids, esters, anhydrides, acidic chlorides, amides, sulfoxides, and phosphine oxides comprising contacting said organic compound with at least a stoichiometric amount of a mixed alkoxy-hydride compound of the formula M[AlH$_{4-n}$(OR)$_n$]$_2$ which may be complexed with a Lewis base, wherein M is an alkaline earth metal, R is selected from an aliphatic, cycloaliphatic or aromatic group having 1 to 20 carbon atoms an n is a number between 0.5 and 3.5 in the presence of an inert organic solvent.

2. The method according to claim 1 wherein R is selected from an alkyl, cycloalkyl, or aryl group.

3. The method according to claim 2 wherein R is an alkyl group having 3 to 8 carbon atoms.

4. The method according to claim 1 wherein R is CH$_2$ CH$_2$ OCH$_3$.

5. The method according to claim 1 wherein said solvent is selected from ethereal, or an aliphatic or aromatic hydrocarbon solvent.

* * * * *

UNITED STATES PATENT AND TRADEMARK OFFICE
CERTIFICATE OF CORRECTION

PATENT NO. : 4,299,986
DATED : November 10, 1981
INVENTOR(S) : Salvatore Cucinella It is certified that error appears in the above—identified patent and that said Letters Patent is hereby corrected as shown below:

Claim 1, line 10 cancel "an" and insert

-- and --

Claim 4, line 2 correct the formula to read

-- $-CH_2CH_2OCH_3$ --

Signed and Sealed this

Sixth Day of April 1982

[SEAL]

Attest:

GERALD J. MOSSINGHOFF

Attesting Officer

Commissioner of Patents and Trademarks